(12) United States Patent
Forsell

(10) Patent No.: US 9,541,552 B2
(45) Date of Patent: Jan. 10, 2017

(54) BLOOD ANALYZING DEVICE FOR MALARIA ANALYSIS

(71) Applicant: Tommy Forsell, Uppsala (SE)

(72) Inventor: Tommy Forsell, Uppsala (SE)

( * ) Notice: Subject to any disclaimer, the term of this patent is extended or adjusted under 35 U.S.C. 154(b) by 0 days.

(21) Appl. No.: 14/649,179

(22) PCT Filed: Dec. 2, 2013

(86) PCT No.: PCT/SE2013/051424
§ 371 (c)(1),
(2) Date: Jun. 2, 2015

(87) PCT Pub. No.: WO2014/088494
PCT Pub. Date: Jun. 12, 2014

(65) Prior Publication Data
US 2015/0316564 A1 Nov. 5, 2015

(30) Foreign Application Priority Data

Dec. 3, 2012 (SE) ..................... 1251363

(51) Int. Cl.
*G01N 33/00* (2006.01)
*G01N 33/569* (2006.01)
(Continued)

(52) U.S. Cl.
CPC ........ *G01N 33/56905* (2013.01); *G01N 21/31* (2013.01); *G01N 33/726* (2013.01); *G01N 2333/445* (2013.01)

(58) Field of Classification Search
None
See application file for complete search history.

(56) References Cited

U.S. PATENT DOCUMENTS 5,827,681 A 10/1998 Krug et al.
7,236,236 B2 6/2007 Hanaoka et al.
(Continued)

FOREIGN PATENT DOCUMENTS

GB 2270752 A 3/1994
WO 02/50518 A2 6/2002
(Continued)

OTHER PUBLICATIONS

Padia et al., Sensitivity of Laser Light Depolarization Analysis for Detection of Malaria in Blood Samples, Journal of Medical Microbiology, 54: 449-452 (2005).
(Continued)

*Primary Examiner* — Jill Warden
*Assistant Examiner* — Brittany Fisher
(74) *Attorney, Agent, or Firm* — Porter Wright Morris & Arthur LLP

(57) ABSTRACT

A blood analyzing device (100) comprises a light source (120) arranged to generate light (40) of a wavelength at which a Hb species in a hemolyzed blood sample (30) has absorbance. A detector system (130) is arranged to detect output light (50) from the sample (30) and generate a Hb signal representative of an amount of the Hb species in the sample (30) and a parasite signal representative of an amount of malaria parasites in the sample (30). A processor (140) generates a red blood cell value based on the Hb signal and generates a parasitemia value based on the parasite signal and the red blood cell value. A display (160) displays the parasitemia value representing a percentage of the red blood cells that are infected by malaria parasites.

23 Claims, 5 Drawing Sheets

(51) Int. Cl.
*G01N 21/31* (2006.01)
*G01N 33/72* (2006.01)

(56) References Cited

U.S. PATENT DOCUMENTS

| | | | |
|---|---|---|---|
| 7,354,775 | B2 | 4/2008 | Yoshida et al. |
| 2002/0041166 | A1* | 4/2002 | Grubisic ............ A61B 5/14532 315/291 |
| 2006/0223137 | A1 | 10/2006 | Yoshida et al. |
| 2007/0002309 | A1* | 1/2007 | Yamamoto ........... G01N 21/253 356/39 |
| 2007/0020721 | A1* | 1/2007 | Yoshida ............. G01N 15/1459 435/34 |
| 2009/0318784 | A1 | 12/2009 | Newman et al. |
| 2010/0261197 | A1 | 10/2010 | Goldberg et al. |
| 2011/0053210 | A1 | 3/2011 | Matsumoto et al. |
| 2011/0053212 | A1 | 3/2011 | Matsumoto et al. |

FOREIGN PATENT DOCUMENTS

| | | |
|---|---|---|
| WO | 2006/104451 A1 | 10/2006 |
| WO | 2006/130921 A1 | 12/2006 |
| WO | 2011/123070 A1 | 10/2011 |
| WO | 2012/158638 A1 | 11/2012 |

OTHER PUBLICATIONS

Yoo et al., Short Report: Automated Detection of Malaria-Associated Pseudoeosinophilia and Abnormal WBC Scattergram by the Sysmex XE-2100 Hematology Analyzer: A Clinical Study with 1,801 Patients and Real-Time Quantitative PCR Analysis in Vivax Malaria-Endemic Area, Am. J. Trop. Med. Hyg., 82(3), pp. 412-414 (2010).

Bernard Nkrumah et al., Hemoglobin estimation by the HemoCue portable hemoglobin photometer in a resource poor setting, BMC Clinical Pathology, 11(5):1-6 (May 12, 2011).

Paul C. Chikezie et al., Studies of Methemoglobin Concentrations of Three Human Erythrocyte Genotypes (Hb AA, Hb AS, and Hb SS) in the Presence of Five Antimalarial Drugs, IJBC, 4:151-157 (Jan. 2009).

Official Action from corresponding European Application No. 13860549.8, dated May 4, 2016.

\* cited by examiner

BLOOD ANALYZING DEVICE FOR MALARIA ANALYSIS

TECHNICAL FIELD

The present embodiments generally relate to blood analyzing devices, and in particular to such blood analyzing devices that can be used to determine parasitemia values from blood samples taken from patients infected by malaria parasites or suspected to be infected by malaria parasites.

BACKGROUND

Malaria is a common and still increasing infectious disease in many countries. Malaria affects the red blood cells in a complex system of propagation of the mosquito *Anopheles*. Sporozoites invade the red blood cells (erythrocytes) and eventually rapture the red blood cells. The effect of malaria is, among others, the destruction of the red blood cells causing anemia in the patient.

Today, microscopy is the gold standard for determination of malaria burden and the effect of treatment thereof. The microscopy methods used are so-called thin layer and thick layer methods. The thin layer method is defined by a single layer of red blood cells, whereas the thick layer method uses hemolyzed red blood cells corresponding to 10-20 layers of red blood cells.

Thin layer microscopy by a skilled operator can morphologically identify the parasite to the species level and determine the percentage of the red blood cells that are infected. The number of such red blood cells containing parasites, as seen as "black dots", in relation to the total number of red blood cells is calculated and used as degree of malaria or malaria burden.

The thick layer method is considered to be the more sensitive method. A defined layer or volume of blood is hemolyzed and the free parasites in a certain area or portion of the blood sample are counted. The disadvantage of this method is that red blood cells cannot be counted due to the hemolyzation. In order to get a measure or estimate of the malaria burden and to follow the effect of any malaria treatment, it is necessary to determine the concentration of the red blood cells.

The above described so-called thin or thick layer methods for determining the degree of the malaria burden require usage of a microscope and a skillful user. In addition, both methods are furthermore quite time consuming.

Malaria diagnosis can furthermore be done by immunological point-of-care (POC) rapid in vitro diagnostic tests. These tests are more costly and are generally not able to directly give information of the degree of malaria burden. Hence, the microscopy methods are the preferred methods in those countries where malaria is most frequent.

WO 2011/123070 discloses determination of the percentage of the red blood cells in a blood sample that are infected by malaria parasites. The disclosed technique uses a flow cytometer together with nucleic acid dyes that react with DNA or react with DNA and RNA and antibodies coupled to a fluorophore and capable of selectively binding to a marker present on leukocytes.

The prior art method of determining a parasitemia value in WO 2011/123070 is marred by a rather complex set-up requiring several chemicals and cumbersome detection equipment.

Hence, there is a need for an efficient solution to determine, preferably automatically determine, parasitemia values for patients infected by malaria parasites and that can be used outside of clinical laboratories.

SUMMARY

It is a general objective to provide a blood analyzing device configured to determine a percentage of red blood cells in a blood sample of a patient that are infected by malaria parasites.

This and other objectives are met by embodiments disclosed herein.

An aspect of the embodiments relates to a blood analyzing device comprising a holder arranged to carry a container having a cuvette comprising a hemolyzed blood sample. A light source is arranged to generate input light of at least one wavelength at which a hemoglobin (Hb) species has absorbance. The input light from the light source is directed into the hemolyzed blood sample. The blood analyzing device also comprises a detector system arranged to detect output light from the hemolyzed blood sample. The detector system is configured to generate a Hb signal and a parasite signal based on the output light. The Hb signal is representative of an amount of the Hb species in the hemolyzed blood sample. The parasite signal is representative of an amount of malaria parasites in the hemolyzed blood sample. A processor is configured to process the Hb signal to generate a red blood cell value representative of a concentration of red blood cells in the blood sample prior to hemolyzis. The processor is also configured to generate a parasitemia value based on the parasite signal and the red blood cell value. A display is arranged to display this parasitemia value representing a percentage of the red blood cells in the blood sample that are infected by a respective malaria parasite.

Another aspect of the embodiments relates to the use of a blood analyzing device as defined above for determining a parasitemia value representative of a percentage of red blood cells in a blood sample that are infected by a respective malaria parasite.

A further aspect of the embodiments relates to a method for determining a parasitemia value for a hemolyzed blood sample. The method comprises positioning a container having a cuvette comprising a hemolyzed blood sample in a holder of a blood analyzing device as defined above. A parasitemia value representative of a percentage of red blood cells in the blood sample that are infected by a respective malaria parasite is read from a display of the blood analyzing device.

The present embodiments enable an automatic determination of the degree of malaria of a patient using a blood analyzing device that can be operated even by non-medical personnel. The embodiments therefore enable an efficient, inexpensive and very fast determination of the degree of malaria burden. The blood analyzing device of the embodiments can be used also outside of healthcare facilities, enabling malaria determination of patients at their homes or at other places remote from healthcare facilities.

BRIEF DESCRIPTION OF THE DRAWINGS

The embodiments, together with further objects and advantages thereof, may best be understood by making reference to the following description taken together with the accompanying drawings, in which.

DETAILED DESCRIPTION

Figure 1:
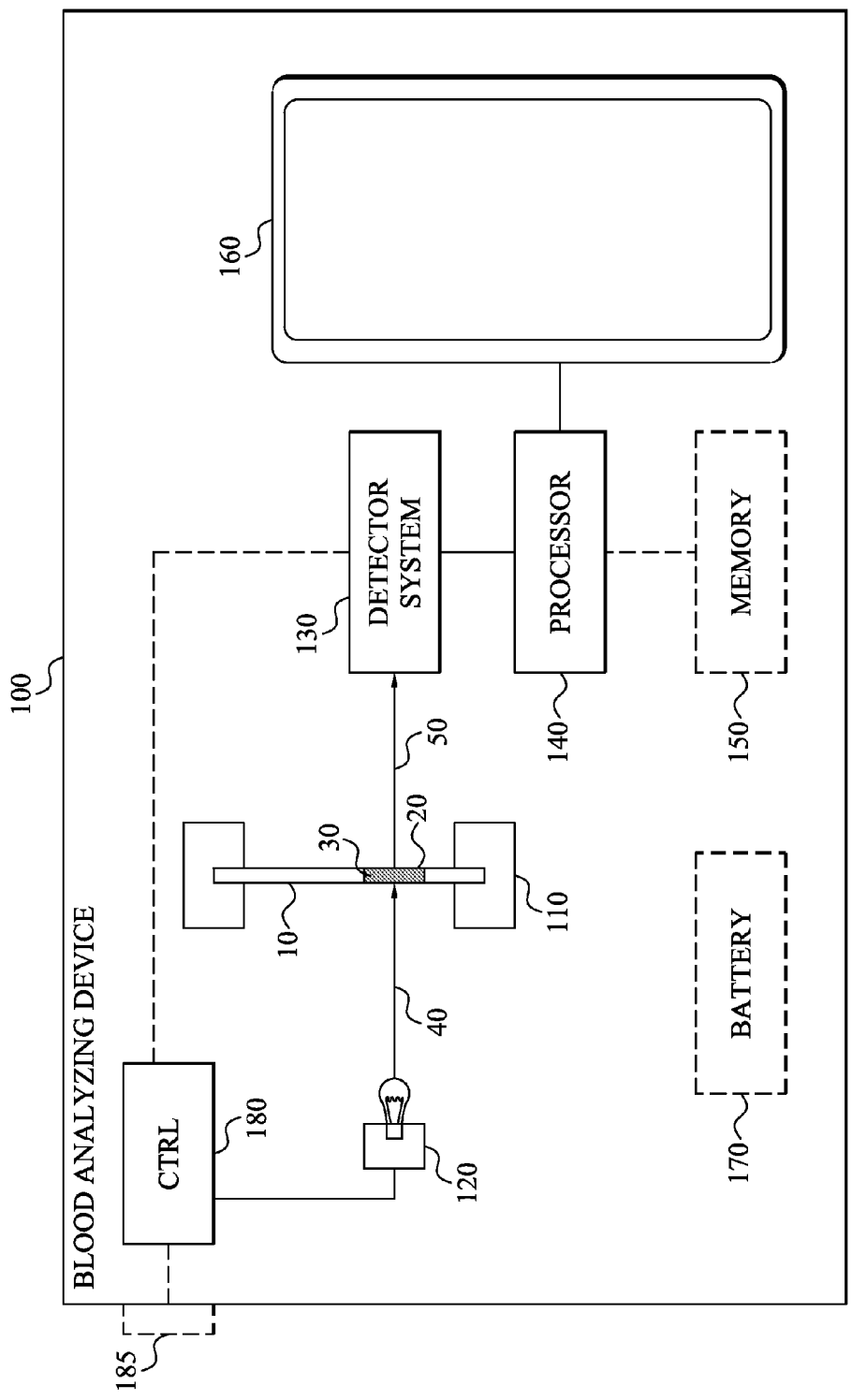
FIG. 1 is a schematic overview of a blood analyzing device according to an embodiment.

Throughout the drawings, the same reference numbers are used for similar or corresponding elements.

The present embodiments generally relate to blood analyzing devices, and in particular to such blood analyzing devices that can be used to determine parasitemia values from blood samples taken from subjects infected by malaria parasites or suspected of suffering from malaria.

The blood analyzing device of the embodiments provides several significant advantages as compared to prior art techniques of determining the degree of malaria burden, i.e. the parasitemia value or the malaria parasite load in a patient. For instance, the blood analyzing device can be run by substantially any person and does not require extensive medical knowledge or experience with malaria diagnosis. Furthermore, the blood analyzing device displays the parasitemia value within a very short period of time, thereby informing the user of the percentage of the red blood cells in a blood sample taken from a patient that are infected by malaria parasites. The blood analyzing device is also configured to automatically generate the parasitemia value once a container with the blood sample has been introduced into a holder of the blood analyzing device, and optionally after activating a user input. Hence, there is not need for laborious manual process steps or manual microscopy-based counting of any malaria parasites in order to get the parasitemia value.

The blood analyzing device of the embodiments can also be used outside of healthcare facilities, such as out in the field in local malaria testing centers or even at the homes of patients. This is possible since no microscope equipment or complex chemicals and flowcytometers are needed. The blood analyzing device is therefore advantageously portable and can be carried by a user.

As used herein, malaria parasite relates to any type of microorganism (parasite) of the genus *Plasmodium* that is capable of causing malaria in humans and/or other animals, preferably other mammals. In particular, malaria parasites encompass parasites of *P. falciparum, P. vivax, P. ovale, P. malariae* and P. knowlesi.

Malaria is, which is well known, a mosquito-borne infectious disease in which the mosquito injects sporozoites when feeding blood from a human or animal. Such a sporozoite infects a liver cell forming a schizont, which is ruptured releasing a multitude of merozoites into the blood. A merozoite may infect a red blood cell forming a trophozoite. The trophozoite undergoes schizogony and develops into a schizont that ruptures the red blood cell releasing a multitude of merozoites that may infect new red blood cells. A merozoite may alternatively infect a red blood cell forming a gametocyte that in turn can infect a new mosquito feeding on the malaria infected human or animal.

Malaria parasite as used herein relates to malaria parasites of the above-mentioned microorganisms in any infectious stage in which the malaria parasite is capable of infecting red blood cells or is present within a red blood cells. Hence, malaria parasites can be present as merozoites, trophozoites, gametocytes or any other form or stage that the malaria parasite may undergo in the red blood cells of the human or animal body.

A general embodiment relates to a blood analyzing device comprising a holder arranged to carry a container having a cuvette comprising a hemolyzed blood sample. A light source is arranged to generate input light of at least one wavelength at which a hemoglobin (Hb) species has absorbance. The input light is directed into the hemolyzed blood sample when the container is carried by the holder. The blood analyzing device also comprises a detector system arranged to detect output light from the hemolyzed blood sample. The detector system is configured to generate a Hb signal representative of an amount of the Hb species in the hemolyzed blood sample based on the output light. The detector system is also configured to generate a parasite signal representative of an amount of malaria parasites in the hemolyzed blood sample based on the output light. A processor of the blood analyzing device is configured to process the Hb signal to generate a red blood cell value representative of a concentration of red blood cells in the blood sample prior to hemolysis. The processor is further configured to generate a parasitemia value based on the parasite signal and the red blood cell value. This parasitemia value is representative of a percentage of the red blood cells in the blood sample that are infected by a respective malaria parasite. The blood analyzing device further comprises a display or screen arranged to display the parasitemia value generated by the processor.

Further implementation examples of this general embodiment of the blood analyzing device will now be described in more detail with reference to the drawings.

FIG. 1 illustrates an embodiment of a blood analyzing device 100. The blood analyzing device 100 comprises a holder 110 arranged to carry a container 10 having a cuvette 20 comprising a hemolyzed blood sample 30. The cuvette 20 is generally in the form of a so-called microcuvette in that the total size of the cuvette 20 and the hemolyzed blood sample 30 is very small, generally comprising one or a few microliters of blood.

The blood analyzing device 100 also comprises a light source 120 arranged to generate input light 40 that is directed from the light source 120 into the hemolyzed blood sample 30 when the container 10 is arranged in the holder 110. The light source 120 is configured to generate light 40 of at least one wavelength at which a hemoglobin (Hb) species in the hemolyzed blood sample 30 has absorbance.

In a particular embodiment, the at least one wavelength could be a wavelength for which Hb (one of the Hb species or bilirubin) in the hemolyzed blood sample 30 has maximum absorbance or at least close to maximum absorbance. Hb can be present in one of the multiple species. In the art, the main such Hb species are oxyhemoglobin ($HbO_2$), carboxyhemoglobin (HbCO), methemoglobin or hemoglobin (Hi), reduced hemoglobin (Hb) and sulfhemoglobin (SHb). As is known in the art, SHb has maximum absorbance close to 625 nm, $HbO_2$ close to 540 nm and 577 nm, HbCO close to 538 nm and 570 nm, Hb close to 555 nm and Hi close to 500 nm. The input light 40 provided by the light source 120 is therefore preferably selected to have a wavelength equal to or close to any of these maximum absorbance wavelengths or could have a band or spectrum of wavelengths covering any of these maximum absorbance wavelengths. Particularly preferred forms of Hb include oxygenated and deoxygenated forms of Hb, i.e. oxyhemoglobin and reduced hemoglobin.

A detector system 130 is arranged in the blood analyzing device 100 to detect output light 50 from the hemolyzed blood sample 30. In a particular embodiment, the detector system 130 is arranged to detect output light 50 having passed through the hemolyzed blood sample 30.

The detector system 130 is arranged to generate a Hb signal representative of an amount of the Hb species in the hemolyzed blood sample 30 based on the detected output light 50. The detector system 130 also generates a parasite signal representative of an amount of malaria parasites in the hemolyzed blood sample 30 based on the output light 50.

The Hb signal and the parasite signal generated by the detector system 130 are input to a connected processor 140. This processor 140 is configured to process the Hb signal to generate a red blood cell value representative of a concentration of red blood cells in the blood sample prior to hemolysis. Thus, the Hb signal is used by the processor 140 in order to generate the red blood cell value according to a preprogrammed relationship or function between the concentration of red blood cells and the Hb concentration: concentration of red blood cells=function (Hb).

The processor 140 is furthermore configured to generate a parasitemia value based on the parasite signal and the generated red blood cell value. This parasitemia value is representative of a percentage of the red blood cells in the blood sample that are infected by a respective malaria parasite. In a particular embodiment, the parasitemia value represents a quotient between the number of malaria parasites as obtained from the parasite signal and the (total) number of red blood cells as obtained from the red blood cell value.

The generated parasitemia value is sent to a connected display or screen 160 that displays the parasitemia value to the user of the blood analyzing device 100. The display 160 could be in the form of any display or screen capable of presenting the parasitemia value to the user. The display 160 could, for instance, be any of a simple screen to more a complex display device, such as a touch-sensitive screen.

In addition to displaying the parasitemia value on the display 160, the processor 140 can be configured to store the generated parasitemia value in a connected memory 150. This stored parasitemia value can then later on be retrieved from the memory 150 by the processor 140 and displayed on the display 160. Alternatively, or in addition, the processor 140 could output the stored parasitemia value from the memory 150 onto a portable memory device, such as USB memory, connected to the blood analyzing device 100 or to an external device that could be connected to the blood analyzing device 100.

The memory 150 could in addition be configured to store the predefined relationship or function that is used by the processor 140 to generate the red blood cell value based on the Hb signal.

The detector system 130 of the blood analyzing device 100 is preferably implemented as a single detector or sensor having dual detector surfaces. Thus, the detector system 130 could then comprise a first dedicated detector surface for detection of the output light 50 and where this detected output light 50 is used to generate the Hb signal and a second dedicated surface for detection of the output light 50 and where this detected output light is used to generate the parasite signal. In a particular embodiment, the first detector surface is in the form of a light intensity measuring detector surface arranged to detect the output light 50 and to generate the Hb signal. The second detector surface is preferably in the form of a pixel detector surface comprising a multitude of photodetectors and is arranged to detect the output light 50 and to generate the parasite signal.

Figure 5:
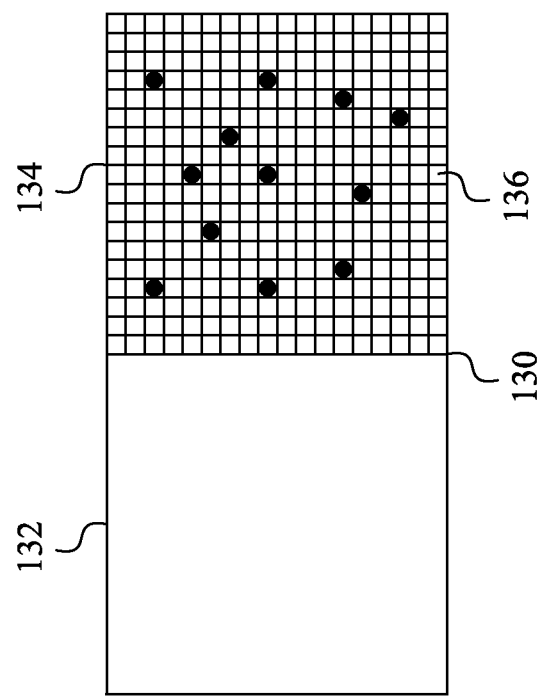
FIG. 5 illustrates an embodiment of a detector system that can be used in the blood analyzing device of FIG. 1.

FIG. 5 is a schematic illustration of a detector system 130 having a light intensity measuring detector surface 132 and a pixel detector surface 134. The light intensity measuring detector surface 132 is preferably configured to measure light intensity at at least one wavelength at which the Hb species has absorbance, preferably has maximum absorbance or close to maximum absorbance. In such a case, the light intensity measuring detector surface 132 generates the Hb signal representing this light intensity at the at least one wavelength.

There are various embodiments of how the light intensity measuring detector surface 132 could generate the Hb signal and the light intensity based on the output light 50 from the hemolyzed blood sample 30.

In a first embodiment, the light source 120 is a broadband light source 120 arranged to provide input light at least in a wavelength range or interval from a first wavelength to a second wavelength into the hemolyzed blood sample 30. The light intensity measuring detector surface 132 is then configured to detect output light 50 in the wavelength range from the first wavelength to the second wavelength from the hemolyzed blood sample 30 and generate the Hb signal based on the detected light intensity of the output light 50 in the wavelength range.

The light intensity measuring detector surface 132 could then operate as a photometer arranged for detecting the total light intensity of the output light 50 within the wavelength range. In an alternative embodiment the light intensity measuring detector surface 132 operates as a spectrophotometer arranged to detect light intensity of the output light 50 at one or, preferably, at a multitude of, advantageously, consecutive wavelengths within the wavelength range.

In a particular embodiment, the light source 120 is configured to output white input light 40. In such a case, at least one filter 126, see FIG. 3, could be arranged in a light path 122 between the light source 120 and the hemolyzed blood sample 30 when the container 10 is positioned in the holder 110 and/or in a light path 124 between the hemolyzed blood sample 30 when the container 10 is positioned in the holder 110 and the detector system 130. This at least one filter 126 can then be used to substantially remove light having a wavelength beyond the wavelength range (first to second wavelength) from the input light 40 and/or the output light 50.

The at least one filter 126 could, for instance, be in the form of a band-pass filter passing light wavelengths within the wavelength range and rejecting (attenuating) wavelengths outside this wavelength range. Alternatively, a low-pass filter can be used together with a high-pass filter to achieve the rejection of wavelengths outside the wavelength range.

In a particular embodiment, the wavelength range from the first to the second wavelength encompasses at least a portion of a spectrum of green light. For instance, the first wavelength could be a wavelength in the interval of from 520 to 560 nm, preferably 530 to 550 nm and more preferably substantially at 540 nm. The second wavelength could be a wavelength in the interval of from 550 to 590 nm, preferably 560 to 580 nm and more preferably substantially at 570 nm with the proviso that the second wavelength is longer than the first wavelength. Hence, an example of suitable wavelength range is within 520 to 590 nm, preferably within 530 to 580 nm and more preferably within 540 to 570 nm.

In a further particular embodiment, the first wavelength and the second wavelength could be selected so that total light absorbance of reduced Hb present in the hemolyzed blood sample 30 within the wavelength range relative to total light absorbance of oxyhemoglobin present in the hemolyzed blood sample 30 within the wavelength range is from 0.8:1 to 1.2:1, preferably from 0.9:1 to 1.1:1, and more preferably substantially 1:1.

Figure 4:
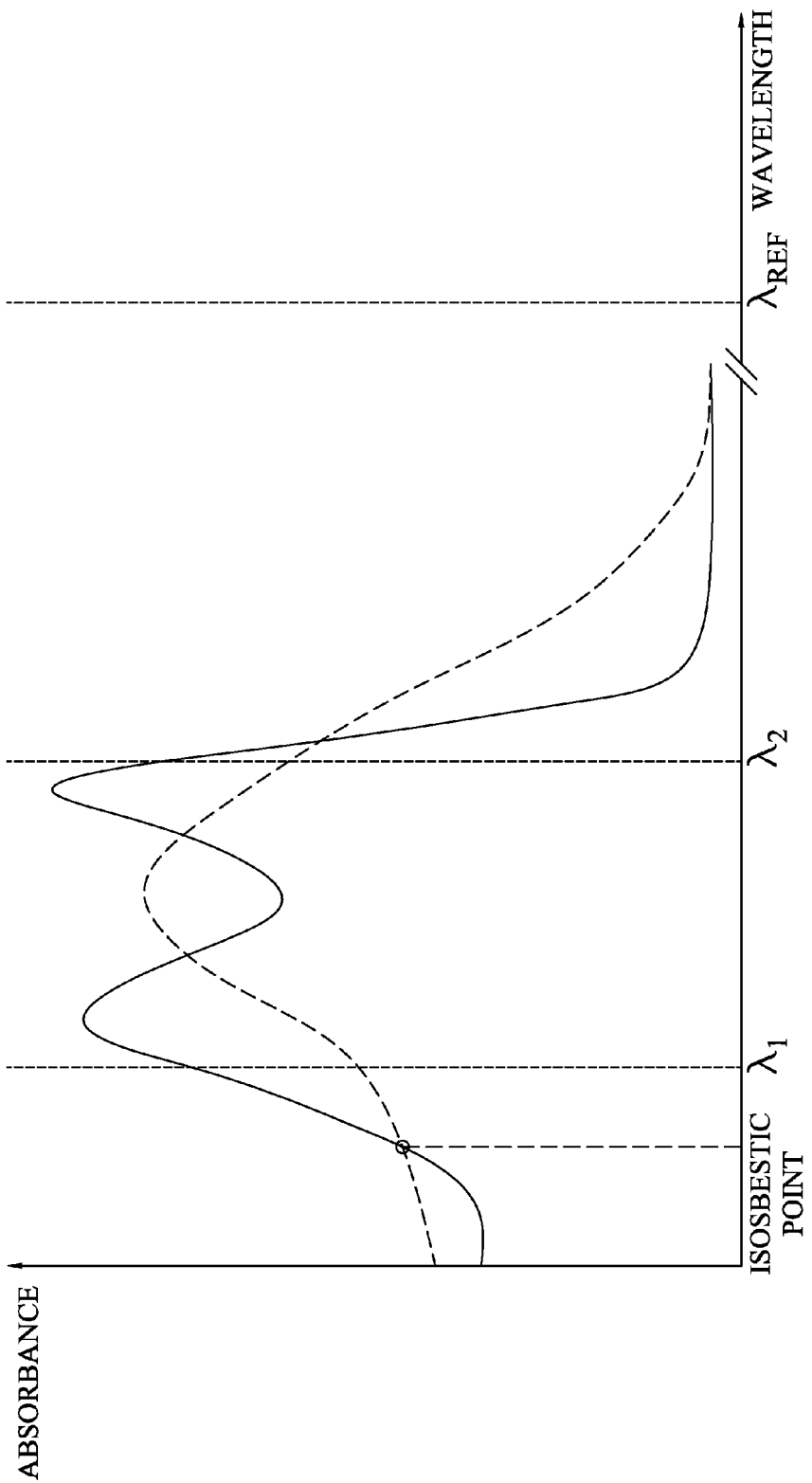
FIG. 4 is a diagram illustrating absorbance of oxygenated and deoxygenated forms of hemoglobin at different wavelengths.

FIG. 4 is a diagram illustrating absorbance of oxygenated (unbroken line) and deoxygenated (broken line) forms of hemoglobin at different wavelengths. The figure schematically illustrates the first wavelength ($\lambda_1$) and the second wavelength ($\lambda_2$) and the wavelength range between these two wavelengths.

Figure 3:
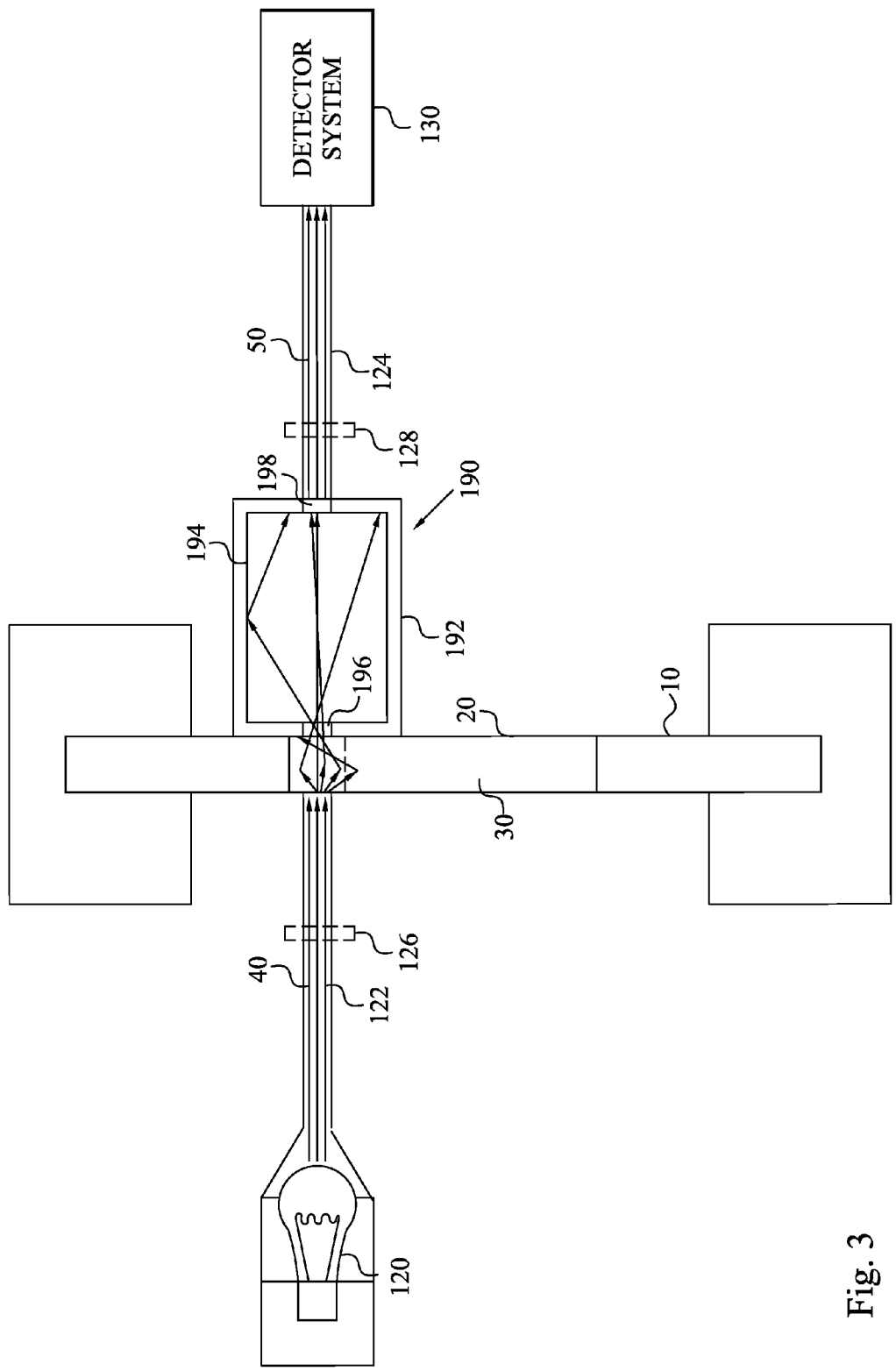
FIG. 3 schematically illustrates a portion of the light emitting, conducting and detecting path of the blood analyzing device according to an embodiment.

In an embodiment, when using a light source 120 in the form of a broadband light source 120, the blood analyzing device 100 optionally comprises a light trap 190 as shown in FIG. 3. The light trap 190 is preferably arranged in the light path 124 of the output light 50 from the hemolyzed blood sample 30 when the container 10 is carried by the holder 110 and the detector system 130. For instance, the light trap 190 can be arranged in connection with the side of the cuvette 20 opposite to the side at which the input light 40 enters the hemolyzed blood sample 30.

The light trap 190 is arranged to reduce an amount of scattered, i.e. non-parallel, light in the output light 50 having passed through the hemolyzed blood sample 30. Such a light trap 190 can be designed in the form of a cylinder 192 of light absorbing material or at least having non-reflective or light-absorbing inner walls. The cylinder 192 has concentrically placed entry and exit holes 196, 198 of a respective diameter that is smaller than the inner diameter of the cylinder 192. Furthermore, the length of the cylinder 192 could be in the range of 5 to 30 times the diameter of the entry and exit holes 196, 198. The substantially parallel (non-scattering) output light 50 exits the light trap 190 and may be guided up to the detector system 130 by the light guide 124. Removal of the scattered light from the detected light leads to a simpler determination of the hemoglobin concentration from the detected light intensity, which is thoroughly described in WO 2006/104451.

In another embodiment, the light source 120 is arranged to generate the input light 40 of a wavelength corresponding to an isobestic point for an oxygenated form of the Hb species and a deoxygenated form of the Hb species. The isosbestic point is a specific wavelength at which two chemical species, in this case reduced Hb and oxyhemoglobin, have the same molar absorptivity. FIG. 4 illustrates an example of a specific wavelength that can be used as the isobestic point around 506 nm. Other isobestic points that could be used in this embodiment is close to 590 nm and optionally near 800 nm.

The light intensity measuring detector surface 132 is then arranged to detect the absorbance at the selected isobestic point and generate the Hb signal based on the detected absorbance at this specific wavelength.

In a further embodiment, the holder 110 is arranged to carry the container 10 having the cuvette 20 comprising the hemolyzed blood sample 30 with the Hb species in an azid-methemoglobin form. Thus, the hemoglobin iron has been converted from the ferrous to the ferric state, for instance by sodium nitrite, to form methemoglobin. This methemoglobin is combined with azide to form azid-methemoglobin. In such a case, the light source 120 is arranged to generate the input light 40 of a wavelength of about 570 nm at which azid-methemoglobin has maximum absorbance. The light intensity measuring detector surface 132 is then arranged to detect the light absorbance at this wavelength of about 570 nm.

Regardless of which implementation embodiment for the light source 120, i.e. broadband light source, providing input light 40 at an isobestic point or providing input light 40 at a wavelength at which azid-methemoglobin has maximum absorbance, the light source 120 is preferably arranged to generate the input light 40 with at least one reference wavelength. This at least one reference wavelength is then preferably a wavelength at which the Hb species has substantially no absorbance. For instance, the at least one reference wavelength could be at least one wavelength within the infrared light spectrum, such as from about 750 nm to about 1 mm, typically within a range from about 750 nm or 800 nm up to about 900 nm. FIG. 4 schematically illustrates this concept of using a reference wavelength ($\lambda_{REF}$) preferably beyond the wavelength spectrum within which Hb species has maximum absorbance.

The detector system 130, and preferably the light intensity measuring detector surface 132 of the detector system 130, is arranged to generate a reference signal based on the output light 50. This reference signal is representative of an amount of light absorbance at the at least one reference wavelength by the hemolyzed blood sample 30. The processor 140 is configured to co-process the reference signal and the Hb signal to generate the red blood cell value. In a particular embodiment, the processor 140 is configured to subtract the light absorbance represented by the reference signal from a light absorbance represented by the Hb signal.

Usage of the at least one reference wavelength generally improves the Hb measurements and the accuracy of the generated red blood cell value by compensating for any turbidity in the hemolyzed blood sample 30 and a general light absorbance increase due to the presence of malaria parasites in the hemolyzed blood sample 30.

The light source 120 of the blood analyzing device 100 can be of different embodiments including, but not limited to, LED, laser, flash types.

As mentioned in the foregoing, the pixel detector surface 134 comprises a multitude of photodetectors 136 arranged to detect the output light 50 and to generate the parasite signal. This parasite signal is representative of the percentage of the multitude of photodetectors 136 that detects a respective malaria parasite. FIG. 5 schematically illustrates this concept by showing twelve photodetectors 136 detecting a respective malaria parasite out of a total of, in this example, 324 photodetectors 136. Hence, the multitude of photodetectors 136 could be regarded as detecting a pattern in the output light 50 and where this pattern is in the form of black dots, corresponding to malaria parasites, on a red background, due to the Hb species in the hemolyzed blood sample 30.

In a particular embodiment and as shown in FIG. 3, the blood analyzing device 100 may comprise a lens system 128 of one or more lenses arranged in the light path 124 of the output light 50 from the hemolyzed blood sample 30 when the container 10 is carried by the holder 110 and the pixel detector surface 134 of the detector system 130. The lens system 128 is then arranged to direct output light 50 onto the pixel detector surface 134 so that a malaria parasite as seen by a photodetector 136 of the pixel detector surface 134 has a size that substantially corresponds to a geometrical extension of the photodetector 136. Hence, in a particular embodiment a malaria parasite as seen by a photodetector 136 preferably has a diameter that corresponds to or is slightly smaller or larger than a diameter or side of the photodetector 136. In such an embodiment, a malaria parasite is typically only detected by a single photodetector 136 of the pixel detector surface 134 and is therefore preferably not counted twice. Furthermore, a given photodetector 136 preferably detects at most a single malaria parasite. In such a case, the parasite signal is easily obtained as representing a quotient between the number of the photodetectors 136 that detect a respective malaria parasite and the total number of photodetectors 136 in the pixel detector surface 134.

For instance, a malaria parasite in merozoite stage is approximately 1-5% of the size of a red blood cell, which in turn typically has a diameter of 6-8 µm and a thickness of about 2 µm. A patient suffering from malaria often has about 4-25% of the red blood cells infected by malaria parasites. This means that there is approximately 20.000 to 200.000 malaria parasites in a cuvette 20 with a measuring area of 1 mm² and a cuvette path length of 0.1 mm. If a lens system 128 is used providing, for instance, 10× magnification the photodetectors 136 of the pixel detector surface 134 should detect about 2.000 to 20.000 malaria parasites of a general size of about 0.1 µm.

The detector system 130 could, as was mentioned in the foregoing, be provided as a dual sensor having the light intensity measuring detector surface 132 and the pixel detector surface 134. Such dual sensors are available in the art, for instance from manufactures such as Panasonic, and are today used in digital cameras.

In another approach the detector system 130 comprises a separate light intensity measuring detector and a separate pixel detector. These two detectors are then provided as separate units but are preferably arranged adjacent each other similar to the detector surfaces 134, 136 in FIG. 5.

The input light guide 122 and the output light guide 124 shown in FIG. 3 can be realized as optic fibers or cables. In further embodiments, the light guides 122, 124 could simply be in the form of short passages between the light source 120 and the cuvette 20 and between the cuvette 20 or the optional light trap 190 and the detector system 130.

Figure 2B:
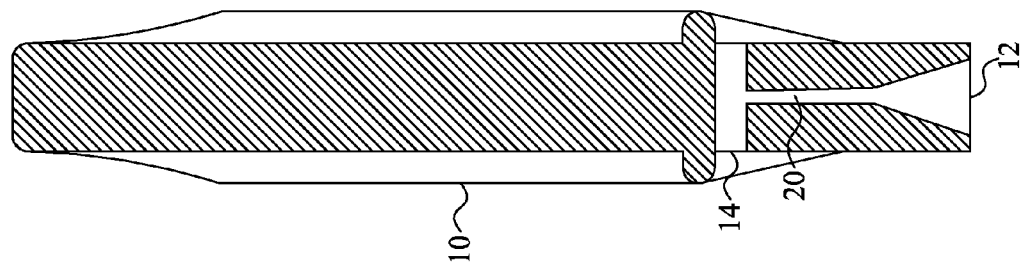
FIG. 2B is a cross-sectional view of the sample container of FIG. 2A along the line A-A.
Figure 2A:
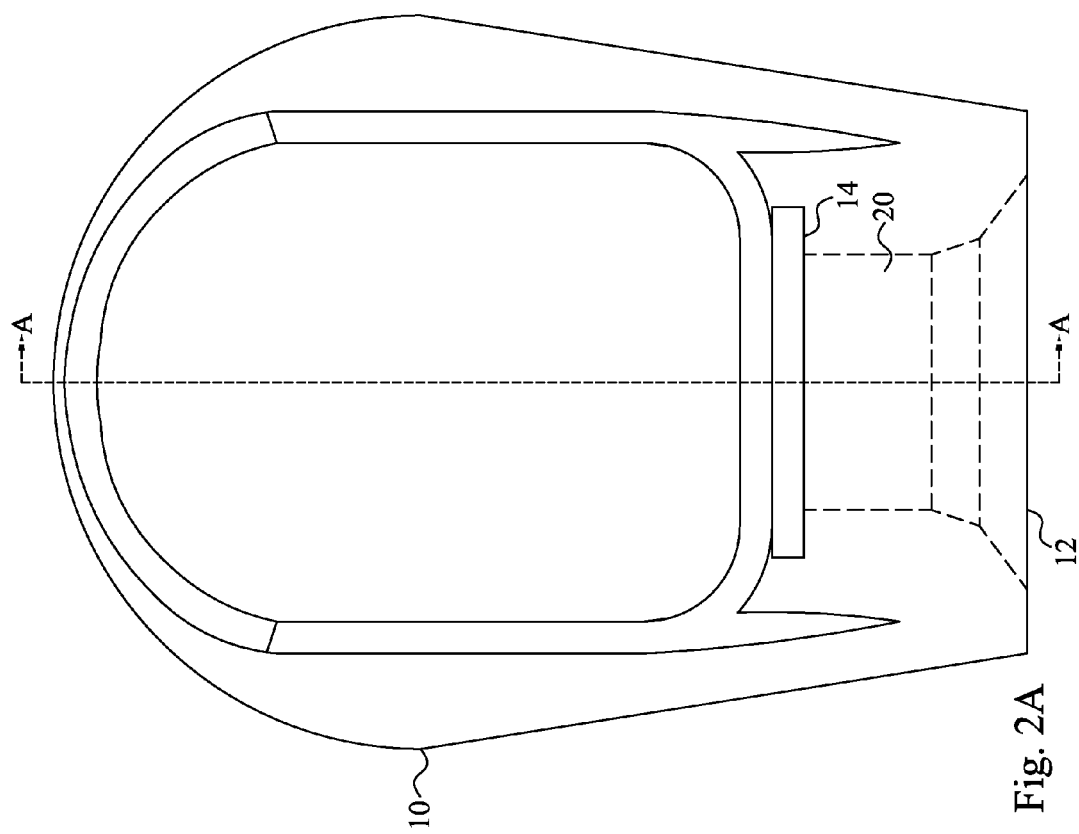
FIG. 2A is a schematic front view of a sample container that can be used in the blood analyzing device according to the embodiments.

FIG. 2A is a frontal view of an example of a container 10 that can be used according to the present embodiments. FIG. 2B is a cross-sectional view of the sample container 10 shown in FIG. 2A taken along the line A-A.

The container 10 comprises a cuvette 20 designed for containing the blood sample to be analyzed by the blood analyzing device 100. An end side of the container 10 comprises an opening 12 that is contacted with blood causing the blood, through the capillary effect, to enter the container 10 and fill up the cuvette 20. The container 10 preferably also comprises an air outlet 14 allowing air present in the cuvette 20 to escape when blood is being drawn into the container 10. The cross-sectional view of the container 10 more clearly illustrates the opening 12 and how it is in contact with the cuvette 20.

The blood analyzing device 100 of the present embodiments is however not limited to usage with a container 10 as illustrated in FIGS. 2A and 2B but can be used in connection with other container and cuvette designs. Generally, the container could have a size of one up to a few square centimeters. The cuvette 20 is generally in the form of a rectangular parallelepided box (cuboid) or a cylinder, though other forms are still possible. The height and width of the cuvette 20 could, for instance, be in the range of 1-10 mm, such as about 5 mm. The thickness could be about 0.01-1 mm, such as about 0.05-0.5 mm. A total volume of the cuvette 20 is typically in the range of 1-10 µl.

The blood sample to be analyzed by the blood analyzing device 100 could be hemolyzed prior to filling the cuvette 20 of the container 10. In such a case, a hemolyzing agent is added to the blood sample causing disintegration and rupture of the erythrocyte membranes releasing the hemoglobin into the sample solution. In an alternative approach, at least a part of an inner wall in the container 10, such as the inner walls of the opening 12 and leading up to the cuvette 20, could be coated with a hemolyzing agent. In such a case, the blood is, when drawn into the cuvette 20, exposed to the hemolyzing agent causing lysis of the membranes of the red blood cells and release of the hemoglobin. A non-limiting example of a hemolyzing agent that can be used according to the embodiments include sodium deoxycholate, which is the sodium salt of deoxycholic acid. Providing hemolyzing agents in dried form in a cuvette 20 is well known in the art and disclosed, for instance, in WO 2008/030154; WO 2008/010760; WO 2006/096126; U.S. Pat. Nos. 5,278,047; and 3,198,064.

In an optional embodiment, a coloring or staining agent can be used to stain the malaria parasites in the blood sample. Any such agent traditionally employed for malaria parasite staining could then be used. Non-limiting examples include Giemsa stain, Weight's stain and Field's strain, Warhurst and Williams, Laboratory diagnosis of malaria, *J Clin Pathol,* 1996, 49: 533-538.

The optional coloring or staining agent can be added to the blood sample prior to or following hemolysis. In alternative approach at least a part of the inner wall of the container 10 could be coated with a coloring or staining agent as discussed above in connection with a hemolyzing agent.

It could also be possible to use a substance or composition having both hemolyzing and parasite staining properties. In such a case, only a single agent needs to be added to the blood sample or coated on the inner wall of the container 10 to achieve both hemolysis of the red blood cells and staining of any malaria parasites.

The usage of staining of malaria parasites is optional according to the embodiments since the blood analyzing device 100 will be able to detect any malaria parasites in the hemolyzed blood sample without the usage of any coloring or staining agent.

The measurement and light detection of the blood analyzing device 100 could be started automatically once the container 10 has been placed in the holder 110. In such a case, a controller or control unit 180 can selectively switch on the light source 120 and/or active the detector system 130, see FIG. 1, when the container 10 has been placed in the holder 110.

Instead of having an automatic initiation of the measurements, the blood analyzing device 100 can be equipped with an activation input 185, non-limitedly illustrated in the form of a push button 185 in FIG. 1. The user of the blood analyzing device 100 will then activate the input 185, which causes the generation of an activation signal that is forwarded to the controller 180. The controller 180 activates the light source 120 and the detector system 130 for performing Hb and malaria parasite reading in the hemolyzed blood sample 30.

The blood analyzing device 100 typically comprises a battery 170 or some other power source, providing the power required for operating the other including elements of the blood analyzing device 100. It is anticipated that the battery 170 can be replaced by an external power source, connected to the blood analyzing device 100 through a power cord.

The blood analyzing device 100 of the embodiments can in a simple, fast and cost-efficient way determine a parasitemia value representative of a percentage of red blood cells in a blood sample, preferably in a human blood sample, which are infected by a respective malaria parasite.

The blood analyzing device 100 may in an embodiment perform the detection of any malaria parasites in the hemolyzed blood sample using phase holographic imaging. In such a case, the detector system 100 comprises a detector for phase holographic image detection that generates the parasite signal representative of the amount of malaria parasites in the hemolyzed blood sample. Phase holographic imaging systems are known in the art, such as the HoloMonitor markted by Phase Holographic Imaging.

An aspect of the embodiments relates to a method for determining a parasitemia value for a hemolyzed blood sample 30. The method comprises positioning a container 10 having a cuvette 20 comprising a hemolyzed blood sample 30 in a holder 110 of a blood analyzing device 100 according to the embodiments. The method further comprises reading, from a display 160 of the blood analyzing device 100, a parasitemia value representative of a percentage of red blood cells in the blood sample 30 that are infected by a respective malaria parasite.

In an optional embodiment, the method additionally comprises activating the activation input to start the measurements.

The method is preferably an in vitro method used to analyze various blood samples. These blood samples can be taken from a blood bank or directly from a patient who is diagnosed with or suspected to suffer from malaria.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A blood analyzing device comprising:
   a holder arranged to carry a container having a cuvette comprising a hemolyzed blood sample;
   a light source operable to generate input light of at least one wavelength at which a hemoglobin (Hb) species has absorbance and arranged to direct said input light into said hemolyzed blood sample;
   a detector system arranged to detect output light from said hemolyzed blood sample and operable to generate, based on said output light, i) a Hb signal representative of an amount of said Hb species in said hemolyzed blood sample, and ii) a parasite signal representative of an amount of malaria parasites in said hemolyzed blood sample;
   a processor configured to process said Hb signal to generate a red blood cell value representative of a concentration of red blood cells in said blood sample prior to hemolysis and configured to generate, based on said parasite signal and said red blood cell value, a parasitemia value representative of a percentage of said red blood cells in said blood sample that are infected by a respective malaria parasite; and
   a display operable to display said parasitemia value.

2. The blood analyzing device according to claim 1, wherein said detector system is arranged to detect output light having passed through said hemolyzed blood sample.

3. The blood analyzing device according to claim 1, wherein said detector system comprises:
   a light intensity measuring detector surface arranged to detect said output light and operable to generate said Hb signal; and
   a pixel detector surface comprising a multitude of photodetectors and arranged to detect said output light and operable to generate said parasite signal.

4. The blood analyzing device according to claim 3, wherein said light intensity measuring detector surface is operable to generate said Hb signal based on a detected light intensity at at least one wavelength of said at least one wavelength at which said Hb species has absorbance.

5. The blood analyzing device according to claim 4, wherein said light intensity measuring detector surface is operable to generate said Hb signal based on a detected total light intensity at a band of wavelengths encompassing at least a portion of a spectrum of green light.

6. The blood analyzing device according to claim 3, wherein said pixel detector surface is operable to generate said parasite signal representative of a percentage of said multitude of photodetectors that detects a respective malaria parasite.

7. The blood analyzing device according to claim 3, further comprising a lens system arranged in a light path of said output light from said hemolyzed blood sample when said container is carried by said holder and said pixel detector surface, wherein said lens system is arranged to direct said output light onto said pixel detector surface so that a malaria parasite as seen by a photodetector of said multitude of photodetectors has a size that substantially corresponds to a geometrical extension of said photodetector.

8. The blood analyzing device according to claim 1, wherein said light source is a broadband light source operable to generate said input light of a band of wavelengths encompassing at least a portion of a spectrum of green light.

9. The blood analyzing device according to claim 8, wherein said detector system is operable to generate said Hb signal based on a detected total light intensity at a band of wavelengths encompassing said at least a portion of said spectrum of green light.

10. The blood analyzing device according to claim 8, wherein said broadband light source is operable to generate white input light.

11. The blood analyzing device according to claim 10, further comprising at least one filter arranged in a light path between said broadband light source and said hemolyzed blood sample when said container is carried by said holder and operable to substantially remove light having a wavelength beyond said band of wavelengths from said input light.

12. The blood analyzing device according to claim 10, further comprising at least one filter arranged in a light path between said hemolyzed blood sample when said container is carried by said holder and said detector system and operable to substantially remove light having a wavelength beyond said band of wavelengths from said output light.

13. The blood analyzing device according to claim 1, further comprising a light trap arranged in a light path of said output light from said hemolyzed blood sample when said container is carried by said holder and said detector system, wherein said light trap is operable to reduce an amount of scattered light in said output light having passed through said hemolyzed blood sample.

14. The blood analyzing device according to claim 13, wherein said light trap is a cylinder of light absorbing material having concentrically placed entry and exit holes of a respective diameter that is smaller than an inner diameter of said cylinder.

15. A blood analyzing device, comprising:
- a holder arranged to carry a container having a cuvette comprising a hemolyzed blood sample;
- a light source operable to generate input light of at least one wavelength at which a hemoglobin (Hb) species has absorbance and arranged to direct said input light into said hemolyzed blood sample,
- a detector system arranged to detect output light from said hemolyzed blood sample and operable to generate, based on said output light, i) a Hb signal representative of an amount of said Hb species in said hemolyzed blood sample, and ii) a parasite signal representative of an amount of malaria parasites in said hemolyzed blood sample;
- a light trap arranged in a light path of said output light from said hemolyzed blood sample when said container is carried by said holder and said detector system, wherein said light trap is operable to reduce an amount of scattered light in said output light having passed through said hemolyzed blood sample, wherein said light trap is a cylinder of light absorbing material having concentrically placed entry and exit holes of a respective diameter that is smaller than an inner diameter of said cylinder, and wherein a length of said cylinder is in a range of 5 to 30 times said respective diameter of said entry and exit holes,
- a processor configured to process said Hb signal to generate a red blood cell value representative of a concentration of red blood cells in said blood sample prior to hemolysis and configured to generate, based on said parasite signal and said red blood cell value, a parasitemia value representative of a percentage of said red blood cells in said blood sample that are infected by a respective malaria parasite; and
- a display operable to display said parasitemia value.

16. The blood analyzing device according to claim 1, wherein said light source is operable to generate said input light of a wavelength corresponding to an isobestic point for an oxygenated form of said Hb species and a deoxygenated form of said Hb species.

17. The blood analyzing device according to claim 16, wherein said detector system is operable to generate said Hb signal based on a detected amount of light absorbance at said wavelength corresponding to said isobestic point.

18. The blood analyzing device according to claim 1, wherein
said light source is arranged to generate said input light of a wavelength of about 570 nm.

19. The blood analyzing device according to claim 18, wherein said detector system is operable to generate said Hb signal based on a detected amount of light absorbance at said wavelength of about 570 nm.

20. The blood analyzing device according to claim 1, wherein
said light source is operable to generate said input light with at least one reference wavelength at which said Hb species has substantially no absorbance;
said detector system is operable to generate, based on said output light, a reference signal based on a detected amount of light absorbance at said at least one reference wavelength by said hemolyzed blood sample; and
said processor is configured to co-process said reference signal and said Hb signal to generate said red blood cell value.

21. The blood analyzing device according to claim 20, wherein said processor is configured to subtract a light absorbance represented by said reference signal from a light absorbance represented by said Hb signal.

22. The blood analyzing device according to claim 20, wherein said light source is operable to generate said input light with said at least one reference wavelength within an infrared light spectrum.

23. A method for determining a parasitemia value for a hemolyzed blood sample comprising:
- positioning a container having a cuvette comprising a hemolyzed blood sample in a holder of a blood analyzing device according to claim 1; and
- reading, from a display of said blood analyzing device, a parasitemia value representative of a percentage of red blood cells in said blood sample that are infected by a respective malaria parasite.

* * * * *